United States Patent [19]
Siiman et al.

[11] Patent Number: 5,891,741
[45] Date of Patent: Apr. 6, 1999

[54] ANTIBODY-AMINODEXTRAN-PHYCOBILIPROTEIN CONJUGATES

[75] Inventors: Olavi Siiman, Davie; Cecilia Smith, Miami; Patricia Roth, Pembroke Pines; Alexander Burshteyn, Hialeah; Robert Raynor, Cooper City, all of Fla.

[73] Assignee: Coulter International Corp., Miami, Fla.

[21] Appl. No.: 857,941

[22] Filed: May 16, 1997

[51] Int. Cl.$^6$ .................................................. G01N 33/548
[52] U.S. Cl. .......................... 436/529; 436/547; 436/800; 436/805; 530/391.1; 530/391.3; 530/391.9; 530/391.5
[58] Field of Search ............................... 530/391.1, 391.3, 530/391.9, 391.5; 436/529, 547, 800, 805

[56] References Cited

U.S. PATENT DOCUMENTS

| | | |
|---|---|---|
| 4,520,110 | 5/1985 | Stryer et al. . |
| 4,649,280 | 3/1987 | Holland et al. . |
| 4,859,582 | 8/1989 | Stryer et al. . |
| 4,925,648 | 5/1990 | Hansen et al. ............................ 424/1.1 |
| 5,527,713 | 6/1996 | Bolton et al. . |
| 5,658,741 | 8/1997 | Bolton et al. .............................. 435/7.2 |

OTHER PUBLICATIONS

Nie, Shuming, "Probing Single Molecules and Single Nanoparticles by Surface–Enhanced Raman Scattering," Science, vol. 275, Feb. 21, 1997.
Gouttefangeas, C., "Differential proliferative responses in subsets of human CD28+ cells delineated by BB27 aAB," Intern'l Imm., vol. 6:3, pp. 423–430.
Maiza, H., "A Novel 80–kD Cell Surface Structure Identifies Human Circulating Lymphocytes . . . Activity," J. Exp. Med., vol. 178: Sep. 1993, pp. 1121–1126.
Bensussan, A., "BY55 monoclonal antibody delineates . . . activity," Proc. Natl. Acad. Sci. USA, vol. 91, pp. 9136–9140, Sep. 1994.
Gollob, J.A., "Molecular Interaction between CD58 and CD2 . . . by IL–12," J. Immun., pp. 1886–1893.
Desai, B., "IL–12 Receptor," J. Immun., vol. 148, 3125–3132, No. 10, May 15, 1992.
Oseroff, A.R., "Antibody–targeted photolysis: Selective . . . e6 Conjugates," Proc. Natl. Acad. Sci. USA, vol. 83, pp. 8744–8748, Nov. 1986.
Zola, H., "Detection by Immunofluorescence of surface molecules present in low copy numbers," J. Imm. Methods., 135, 247–255 (1990).
Cohen, J. "Enumeration of CR1 complement receptors . . . antigens by flow cytometry," J. Imm. Methods, 99, 53–58 (1987).
Madri, J., "Use of Avidin–Biotin Complex . . . Antisera," Lab. Invest., vol. 48, No. 1, p. 98, 1983.
Shamsuddin, A., "Improved Enzyme Immunoassays Using Biotin–Avideim–Enzyme Complex," Arch Pathol Lab Med., vol. 107, 514–517 (Oct. 1983).
Adler–Storthz, K., Biotin–Avidin–Amplified Enzyme . . . Clinical Specimens, J. Clin. Microb. Dec. 1983, pp. 1329–1334, vol. 18, No. 6.
Custer, M., "Rapid Fluorescence assay for IL–4 detection in supernatants and serum," J. Imm. Methods, 128, 109–119 (1990).
Gouttefangeas, C., "Delineation of human CD28 functional subsets . . . CDw101," T–Cell antigens, pp. 293–295.

*Primary Examiner*—Christopher L. Chin
*Attorney, Agent, or Firm*—Warren W. Kurz

[57] ABSTRACT

The present application discloses dextran crosslinked, antibody-phycobiliprotein conjugates containing up to twenty phycobiliprotein per dextran molecule which conjugates are able to achieve amplification of fluorescence intensity over direct antibody-phycobiliprotein labeled cells of two fold or greater.

18 Claims, 5 Drawing Sheets

ANTIBODY-AMINODEXTRAN-PHYCOBILIPROTEIN CONJUGATES

BACKGROUND OF THE INVENTION

1. Field of the Invention

This invention generally relates to a novel antibody-dextran-phycobiliprotein conjugate. In particular the present invention relates to a new antibody-aminodextranphycoerythrin conjugate, a method of making said conjugate, and a method for detecting biological substances in an assay using said conjugate.

2. Description of the Prior Art

There has always been a need to develop systems that can accurately and reliably detect and quantitate relatively low levels of biological substances in an assay. The demand for such systems has resulted in the development of a variety of detection methods in which the number of probe molecules per targeted site of interest is amplified, thus making it considerably easier to detect target sites.

For example, enhanced light absorption is used in enzyme immune assays in which substrate absorption is enhanced by large substrate turnovers and use of the high affinity avidin-biotin system See A. M. Shamsuddin and C. C. Harris, *Arch. Pathol. Lab. Med.* 107, 514–517 (1983); Adler-Storthz, et al., *J. Clin. Microbiol.* 18, 1329–1334 (1983); and J. A. Madri and K. W. Barwick, *Lab. Invest.* 48, 98–107 (1983). Enhanced light scatter is obtained in the side scatter from polystyrene beads coated with colloidal gold particles as described in U.S. Pat. No. 5,552,086, issued Sep. 3, 1996 to Siiman et al. Enhanced light emission is used in indirect fluorescence staining of cell receptor sites with multiple layers of phycoerythrin-streptavidin attached to biotinylated antibody at cell receptor sites as described by J. H. M. Cohen et al., *J. Immunol. Methods* 99, 53–58 (1987) and H. Zola et al., *J Immunol. Methods*, 135, 247–255 (1990). Enhanced light-induced photochemistry is used in excitation of chlorin $e_6$ coupled through dextran to anti-T-cell monoclonal antibody to enhance singlet oxygen production as described by A. R. Oseroff et al., *Proc. Natl. Acad. Sci., USA* 83, 8744–8748 (1986). The single, common feature in the above methods is the increase in the number of probe molecules or particles per targeted site.

Increasing the number of probe molecules or particles per targeted site, however, does not always work. For example, H. M. Shapiro describes one attempt at amplification of fluorescence signals by Tomas Hirshfeld et al., at Block Engineering, wherein several hundred fluorescein molecules were attached to a synthetic polymer, polyethylenimine, which was then conjugated with antibody. The method did not work because fluorescence emission from fluorescein molecules was quenched due to the short nearest neighbor distances between fluorophores on the same polymer molecule. See PRACTICAL FLOW CYTOMETRY, 3rd edition, H. M. Shapiro, Wiley-Liss, New York, N.Y., 1995, p. 277.

Fluorescent dextrans have been used for fluorescence amplification, and numerous fluorescent dextrans are commercially available. See HANDBOOK OF FLUORESCENT PROBES AND RESEARCH CHEMICALS, 6th edition, R. P. Haugland, Molecular Probes, Inc., Eugene, Oreg. 97402, 1996. Fluorescent dextrans consist of soluble dextrans (that is, 10,000, 40,000, 70,000, 500,000, and 2,000,000 daltons) conjugated with various fluorescent dyes such as fluorescein, dansyl, rhodamine, and Texas Red. The degrees of substitution in these fluorescent dextrans are 1–2 dye molecules per dextran of 10,000 daltons, 2–4 dye molecules per dextran of 40,000 daltons, 3–6 dye molecules per dextran of 70,000 daltons, about 64 dye molecules per dextran of 500,000 daltons, and about 134 dye molecules per dextran of 2,000,000 daltons. Higher degrees of substitution than these usually lead to quenching and non-specific interactions. Conjugated dextrans are also available as so-called "lysine-fixable", that is, they have incorporated lysine residues which can be used for further reaction, such as covalent attachment of antibody molecules. Fluorescein isothiocyanate (FITC) derivatives of dextran and poly-L-lysine with degrees of substitution ranging from 0.003 to 0.020 molecules of FITC per molecule of glucose and from 0.003 to 0.01 molecule of FITC per molecule of lysyl residue, are commercially available from sources, such as Sigma Chemical Company. For the largest molecular weight dextran listed (2,000,000 daltons) up to 33 to 222 molecules of FITC per molecule of dextran are available; and for a 70,000 dalton poly-L-lysine molecule, up to 5.5 molecules of FITC are available.

Aminodextran of sufficiently large molecular weight can accommodate multiple antibody molecules. The linearity of the polymeric sugar chain of antibody-dextran complexes is an advantage in providing access to targeted antigenic sites on cells without incurring steric hindrance that might occur with a globular polymeric molecule as a carrier. U.S. Pat. No. 5,527,713 issued Jun. 18, 1996, to Bolton et. al., describes the conjugation of anti-CD3 monoclonal antibody to aminodextran (1X-aminodextran, ~1,000,000 daltons, 7% diamine substitution; 5X-aminodextran, ~350,000 daltons, 20% diamine substitution) under saturating conditions of antibody on dextran to give a T3 antibody:aminodextran molar ratio in the conjugates of 37:1 for T3-1X-Amdex and 20:1 for T3-5X-Amdex, thus showing that aminodextran can be effectively loaded with many large protein molecules.

Another attempt at fluorescence amplification uses the fluorescent dye rhodamine. See Shechter et al., *Proc. Natl. Acad. Sci., USA* 75, 2135–2139 (1978). Higher than usual fluorescence intensities were obtained for the peptide hormones insulin and epidermal growth factor, by covalent attachment of these peptides to alpha-lactalbumin molecules that were highly substituted with rhodamine molecules (i.e., 7:1). This was accomplished while still retaining some binding affinity of the hormone for its receptor (which is one of the basic requirements of any process of this kind).

Another currently available family of fluorescent dyes is the phycobiliproteins. The phycobiliproteins are a family of macromolecules found in red algae and blue-green algae. Each phycobiliprotein molecule contains a large number of chromophores. An antibody molecule directly labeled with fluorescein will have between 1 and 3 chromophores associated with it. An antibody molecule directly labeled by conjugation with a phycobiliprotein may have as many as 34 associated chromophores, each with an absorbance and quantum yield roughly comparable to those of fluorescein. Thus, phycoerythrin, (PE), a member of the phycobiliprotein family, is among the brightest fluorescent dyes currently available. Conjugated to an antibody, PE has been used to detect interleukin-4 in a fluorescent plate assay and found in M. C. Custer and M. T. Lotze, *J. Immunol. Methods*, 128, 109–117(1990), to be the only tested fluorophore that produced adequate signal.

In PE there is a monodisperse population of fluorescent groups that are already embedded in a protein. PE exhibits maximal absorbance and fluorescence without susceptibility to either internal or external fluorescence quenching so that attachment of two or more PE molecules to a polymeric carrier should not quench PE fluorescence. The net fluorescence intensity from a PE-polymer complex should be the sum of fluorescence intensities from individual PE molecules. Heretofore, it has not been possible to directly conjugate more than a single PE molecule (MW, 240,000 daltons) to an IgG antibody (MW, 160,000 daltons) without destroying or adversely affecting antibody activity. See U.S. Pat. No. 4,520,110, issued May 28, 1985 to Stryer et al., and U.S. Pat. No. 4,859,582, issued Aug. 22, 1989 to Stryer et al.

On a molar basis, one molecule of PE has a fluorescence yield that is equivalent to at least 30 fluorescein or 100 rhodamine molecules at comparable wavelengths. Thus, one would expect that the largest molecular weight FITC-dextran conjugate with the greatest degree of FITC substitution would have the potential to yield a fluorescence enhancement factor of 222/30=7.4 over a single PE molecule. However, with so many FITC units per dextran carrier and a broad distribution in the molecular weight of each dextran, it is difficult to synthetically mimic the monodisperse population of fluorescent groups that occurs naturally in molecules of PE. The spread in fluorescent intensities from one molecule of FITC-dextran complex to another offsets the large enhancement factor that may be numerically anticipated. With respect to rhodamine, the 7:1 rhodamine-to-carrier molar ratio falls far short of the 100:1 rhodamine to PE ratio needed for equivalent fluorescence intensity.

Therefore, no enhancement factor greater than one, relative to PE fluorescence, to date has been reported for the above FITC derivatives of dextran or poly-L-lysine. This is so, even though other fluorescent dyes are available and one might expect an enhancement factor of 7.4 over a single PE molecule. Thus, there is still a need for the amplification of fluorescence emission signals which uses a direct fluorescent marker to achieve emission intensities greater than those of about 1:1 antibody-PE conjugates.

SUMMARY OF THE INVENTION

In view of the foregoing an object of this invention is to provide a new fluorescent conjugate which achieves emission intensities greater than those achieved by 1:1 antibody-phycobiliprotein conjugates.

Another object is to provide a method for preparing said conjugate.

Yet another object is to provide a method for enhancing the detectability of substances in an assay using said conjugate.

The conjugate of the present invention may be used as a direct method of obtaining two fold or greater amplification of fluorescence signal over direct antibody-phycobiliprotein labeled T lymphocytes.

The conjugate of the present invention may also be used as a method of enhancing fluorescent signals particularly in situations where low density concentration of a receptor molecule exists, and which signals are otherwise difficult to detect.

In satisfaction of the foregoing objects, there is provided by this invention a novel dextran-crosslinked, antibody-phycobiliprotein conjugate containing up to twenty phycobiliprotein per dextran molecule.

Preferably, the dextran component of such a conjugate is 5X-aminodextran or 1X aminodextran; the phycobiliprotein component is R-phycoerythrin; and the anti-body component is selected from the anti-BB27, anti-BY55 and anti IL12 antibody According to another aspect of the present invention there is provided a method for preparing the antibody-aminodextran-phycobiliprotein conjugate of the invention. Such method comprises the steps of:

(a) activating the antibody with iminothiolane, then purifying the activated antibody;

(b) activating the phycobiliprotein with iminothiolane, then purifying the activated phycobiliprotein;

(c) combining the activated and purified antibody and phycobiliprotein;

(d) activating the aminodextran with sulfo-SMCC, then purifying the activated aminodextran;

(e) mixing all activated components together for about 16–24 hours; and (f) purifying the mixture into its components, preferably by size exclusion chromatography.

According to another aspect of the present invention, there is provided a method for detecting biological substances in an assay. Such method comprises the steps of:

(a) mixing an antibody-aminodextran phycobiliprotein conjugate, having a plurality of phycobiliprotein molecules per aminodextran molecule, with a sample containing the substance to be detected, to allow the antibody of such conjugate to couple to the substance to form a complex;

(b) exciting each phycobiliprotein molecule of the complex to cause it to fluoresce by irradiating by, preferably by excitation radiation in order to obtain a fluorescence signal from the complex; and (c) detecting the fluorescence signal from the complex.

Preferably, the fluorescent light emission is measured by flow cytometric analysis.

Other aspects and advantages of the present invention are described further in the following detailed description of the preferred embodiments thereof, reference being made to the accompanying figures.

BRIEF DESCRIPTION OF THE DRAWINGS

Each histogram in FIGS. 1A, 1B, 2A, 2B, 3A, 3B, 3C, 4A, 4B and 5A–5F shows a plot of cell number (vertical axis) versus mean channel fluorescence intensity (horizontal axis).

DETAILED DESCRIPTION OF THE INVENTION

The conjugates of the present invention are dextran crosslinked, antibody-phycobiliprotein conjugates containing up to twenty five phycobiliprotein per dextran molecule. These conjugates are advantageous in that they are able to produce an amplification of fluorescence intensity over direct antibody-phycobiliprotein labeled cells of two fold or greater.

The biliproteins (the term "biliproteins" is equivalent to the term "phycobiliprotein") have a molecular weight of at least about 30,000 daltons, more usually at least about 40,000 daltons, and may be as high as 60,000 or more daltons usually not exceeding about 300,000 daltons.

The biliproteins will normally be comprised of from 2 to 3 different subunits, where the subunits may ranged from about 10,000 to about 60,000 molecular weight. The biliproteins are normally employed as obtained in their natural form from a wide variety of algae and cyanobacteria. The biliproteins may also commercially available from various sources including: Molecular Probes, Inc., Eugene, Oreg. and Prozyme, Inc., San Leandro, Calif. The presence of the protein in the biliproteins provides a wide range of functional groups for conjugation to proteinaceous and non-proteinaceous molecules. Functional groups which are present include amino, thiol, and carboxyl. In some instances, it may be desirable to introduce functional groups, particularly thiol groups when the biliprotein is to be conjugated to another protein.

The number of biliproteins per dextran will depend upon concentrations of activated species during conjugation, degree of activation of species, size and shape of dextran derivative, and size and shape of biliprotein. A number of linking groups may be employed for conjugating the biliprotein to the dextran. There is ample literature for conjugating phycobiliprotein to proteins. See for example Handbook of Fluorescent Probes and Research Chemicals, 6th Ed., R. P. Haugland, Molecular Probes, Inc., Eugene, Oreg., 1996, the description of which are incorporated by reference herein. Examples of commercially available cross-linking reagents are disclosed in the Pierce Catalog and Handbook, Life Science and Analytical Research Products, Pierce Chemical Company, Rockford, Ill., 1994/1995.

Known linking procedures as described in the above publications may be employed. For example, the phycobiliprotein may be activated with 2-iminothiolane to introduce more thiol groups and conjugated to sulfo-SMCC-activated aminodextran.

Examples of phycobiliproteins useful in the present invention are allophycocyanin, phycocyanin, R-phycoerythrin, allophycocyanin B, B-phycoerythrin, phycoerythrocyanin, and b-phycoerythrin, preferably R-phycoerythrin.

Aminodextrans were prepared by methods described in U.S. Pat. No. 5,466,609 issued Nov. 14, 1995 and U.S. Pat. No. 5,527,713 issued Jun. 18, 1996, by periodate oxidation of dextran followed by reaction with 1,3-propanediamine, which teaching are incorporated herein by reference. Of course, the particular method of making the aminodextrans is not limited to such techniques and it is envisioned that any technique for making such aminodextrans is within the practice of the invention. Preferably, the aminodextran is 5X-Amdex and 1X-Amdex, most preferably the aminodextran is 5X-Amdex. The preferred aminodextran has a degree of substitution with 1,3-diaminopropane of $1/8$ or less, but not less than $1/40$, which is the degree of substitution for 1X-Amdex.

As used herein the term "antibody" is defined to include polyclonal antibodies from any native source, and native or recombinant monoclonal antibodies of classes IgG, IgM, IgA, IgD, and IgE, hybrid derivatives, and fragments of antibodies including Fab, Fab' and F(ab')$_2$.

Monoclonal antibodies were obtained by conventional hybridoma methods and purified from ascites fluid by ammonium sulfate (45%) precipitation, centrifugation and affinity chromatography using protein A. The standard process of making monoclonal antibodies is described in G. Kohler and C. Milstein, Nature 256: 495–497 (1975), which teaching are incorporated herein by reference. Of course, the particular method of making and the type of monoclonal antibody is not limited to such techniques and it is envisioned that any technique for making such antibodies is within the practice of the invention.

The monoclonal antibodies BB27, and IL-12 and BY55 were chosen for the dimness (low fluorescence intensity) of their PE conjugate labeled cells, reflecting the low density of antigenic receptors on the surface of the cells. However, any antibody targeting receptor sites on cells may be used, since the amplification of fluorescent intensities using the antibody-dextran-phycobiliprotein conjugate does not depend on the density of receptor sites on a cell. Thus, the selection of the antibody is not a limiting factor in this invention.

The protein-aminodextran conjugates were prepared as described in U.S. Pat. No. 5,527,713, which teaching are incorporated herein by reference, except that two different proteins, one a monoclonal antibody and the other a fluorescent protein (PE) were conjugated simultaneously to the aminodextran.

Preferably, conjugation of antibody and phycobiliprotein to aminodextran is accomplished by activation of PE, activation of antibody, and activation of aminodextran as follows:

(1) a solution of Amdex in distilled water, to which buffer solution was added, was activated with sulfosuccinimidyl 4-[N-maleimidomethyl]cyclohexane-1-carboxylate (sulfo-SMCC) solution in 1×PBS. The mixture was roller mixed for about one hour at room temperature. After the mixing was completed, the reaction mixture was immediately applied to the top of a G-50 Sephadex column equilibrated with 1×PBS. The sample was eluted using 1×PBS and collected in about 2 mL fractions. Fractions of the first band, absorbing at 280 nm, contained the high molecular weight activated Amdex as was verified by Tyndall scatter with a focused visible light beam. These fractions were pooled to give sulfo-SMCC-activated Amdex;

(2) the monoclonal antibody was activated by the addition of a solution of 2-iminothiolane in 1×PBS to antibody concentrate. The resulting solution having an antibody concentration of 15 mg/mL and an iminothiolane-to-antibody molar activation ratio of 15 was mixed at ambient temperature for about one hour. The reaction mixture was then chromatographed on a G-50 Sephadex column equilibrated with 1×PBS and the sample was eluted using 1×PBS. The first band peak fractions were collected and pooled;

(3) phycobiliprotein was activated by the addition of a solution of 2-iminothiolane in 1×PBS. The resulting solution having a phycobiliprotein concentration of 40 mg/mL and an iminothiolane-to-phycobiliprotein molar activation ratio of 22.5 was mixed at room temperature for about one hour. The reaction mixture was then applied to the top of a G-50 Sephadex column equilibrated with 1×PBS and the sample was eluted with 1×PBS ;

(4) iminothiolane-monoclonal antibody solution was first mixed with iminothiolane-phycobiliprotein solution to which a sulfo-SMCC-5X-Amdex solution was subsequently added. The entire mixture was then roller mixed overnight for about 16–24 hours. After the mixing was completed, the total volume of each mixture was determined and 0.120 times this volume of 5 mg/mL L-cysteine in 1×PBS was added to the conjugation mixture. The L-cysteine containing mixtures were then mixed for an about 15 minutes to effect blocking of any unreacted sulfo-SMCC moieties. Lastly, iodoacetamide in 1×PBS in the amount of 0.120 times the total mixture volume and 1M borate buffer solution, pH 9.8, in the amount of 0.020 times the total mixture volume were added to the conjugation mixture. The resulting mixture was mixed for about 30 minutes to block any unreacted sulfhydryl groups;

After blocking, the mixture was purified into its components by size exclusion chromatography as follows: the total volume of the conjugation mixture was reduced to about 1.0 to 1.5 mL. The sample was then applied to the top of a Bio-Gel A-5 m or A-15 m agarose column (2.5 cm×48 cm) equilibrated with 1×PBS and chromato-graphed using 1×PBS as eluant. Eluant fractions of about 4 mL volume were collected. The fractions were monitored at 280 nm. The fractions of the first band collected for the antibody-Amdex-PE conjugate were analyzed spectrophotometrically at 565 and 280 nm using a 1 cm path length cell. The concentration of PE in mg/mL in the conjugate was derived from the absorbance at 565 nm. The active antibody concentration in the conjugate was determined by an ELISA assay.

The conjugates of the present invention may be used in a wide variety of ways. For example, for enhancing known methodologies for the detection, diagnosis, measurement and study of antigens, either present as individual molecules or in more complex organizations, such as viruses, cells, tissue, organelles, e.g. plastids, nuclei, etc.

One of the uses of the subject conjugates is fluorescent staining of cells. The cells may then be observed under a microscope, the presence of the fluorescer being diagnostic of the presence of a specific determinant site or the cells may be detected in a fluorescence-activated cell sorter (FACS). One or more of the biliproteins conjugates may be used, where the fluorescence emission maximum of the biliproteins is separated by at least about 15 nm, preferably by at least about 25 nm. Alternatively, the biliproteins conjugates may be used in conjunction with fluorescers other than biliproteins, for example fluorescein, where the emission maxima are separated by at least about 55 nm, preferably about 58 nm.

By using combinations of fluorescers, one can provide for the detection of subsets of aggregations, such as particular types of cells, strains of organisms, strains of viruses, the natural complexing or interaction of different proteins or antigens, etc. Combinations of particular interest are combinations of fluorescein with biliproteins capable of being activated with the same laser light source. These biliproteins have absorption maxima in the range of about 450 nm to 650 nm, e.g. R-phycoerythrin at 480, 546, and 565 nm.

Another use of the subject conjugates is in immunoassays or competitive protein binding assays, where the subject biliproteins serve as fluorescent labels. Here, the biliprotein conjugate may be conjugated to either a ligand or a receptor, preferably an antibody.

As examples of the utility of the invention, antibodies were chosen to target antigenic sites on biological cells that were normally not abundant, i.e., 10–1000 antigenic receptors per cell, and thus would normally show fluorescence intensities close to or obscured by background fluorescence from cells as measured by flow cytometry.

EXAMPLE I

Preparation of Purified Antibodies

A. BB27 Monoclonal Antibody

BB27 monoclonal antibody, clustered as CD101 in the 5th International Workshop on White Cell Differentiation antigens (*Leukocyte Typing V: White Cell Differentiation Antigens,* eds. Schlossman, S. F., Boumsell, L., Gilks, W., Harlan, J. M., Silverstein, R., Tedder, T. F., and Todd, R. F., (1995), Oxford University Press, Oxford, UK) was obtained by immunization of Balb/c mice with the CD4+CD8+ thymic clone B12. Spleen cells from immunized mice were fused to the NS1 cell line 5 days after the last injection. The initial screening by indirect immunofluorescence and flow cytometry retained all the hybridoma culture supernatants reactive with the immunizing cells but weakly, with the resting PBMC. Cultures containing selected antibodies were cloned twice by limiting dilution (See Gouttefangeas, et al., *Int. Immunol.* 6(3)423, 1994). The cloned hybridoma was injected i.p. into Balb/c mice primed with pristane for ascites production. Antibody was purified from ascites by ammonium sulfate (45%) precipitation, centrifugation and affinity chromatography using protein A-Sepharose. BB27 monoclonal antibody is an IgG1.

The BB27 antigen is expressed on monocytes, resting or activated granulocytes, and some stromal cell lines. It is also expressed on a subpopulation of peripheral blood T cells (29 percent) and some T-cell clones. The T-lymphocyte subset defined by BB27 was further found to contain about one third of CD4+ cells and one half of CD8+ cells. In addition, BB27 was expressed on both CD45RA 'naive' and CD45RO 'memory' T-cell subsets.

B. IL-12Rβ.44 Monoclonal Antibody

IL-12Rβ.44 monoclonal antibody is specific for IL12Rβ.44 recognizes the human IL12 receptor β chain. It was obtained by immunization of BALB/c mice with the mouse cell line 300-19 transfected with the human IL12 receptor β chain (IL-12Rβ) and subsequent fusion of spleen cells with NS1 myeloma cells. Hybridomas supernatants were screened by indirect immunofluorescence and flow cytometry using the immunizing transfectant as the positive cell line and the untransfectant parent line 300-19 as a negative control (See Gollob et. al., *J. Immunol.* 157, 1886, 1996). Ascites was produced in mice injected i.p. with IL-12Rβ.44 hybridoma. Antibody was purified from ascites by ammonium sulfate precipitation (45%), centrifugation and affinity chromatography using Protein A-Sepharose. The antibody is an IgG1.

The IL12Rβ chain is expressed on activated but not resting T cells and NK cells and on T cell clones (See Desai et. al., *J. Immunol.* 148, 3125, 1992).

C. BY55 Monoclonal Antibody

The BY55 monoclonal antibody was obtained by immunizing BALB/c mice with the human NK cell line YT2C2 and subsequent fusion with NS 1 myeloma cells (See Maiza et. al., *J. Exp. Med.* 178 1121, 1993). Hybridoma supernatants were positively screened with the immunizing cells and negatively screened with the T cell clone JF1 and an EBV-transformed B cell line. Cultures containing selected antibodies were cloned twice by limiting dilution. The cloned hybridoma was injected i.p. into Balb/c mice primed with pristane for ascites production. Antibody was purified from ascites fluid by ammonium sulfate precipitation (40%, twice) and size exclusion chromatography on a Sephacryl S300 column. The BY55 antibody is an IgM.

The BY55 antigen is expressed on natural killer (NK) cells, γ/δ T cells and a subpopulation of α/β T cells (See Maiza et. al., *J. Exp. Med.* 178, 1121, 1993). They are also found in cord blood and bone marrow cells which are functionally defined as NK cells and NK cells or cytotoxic lymphocytes, respectively (Bensussan et. al., *Proc. Natl. Acad. Sci. USA*. 91, 9136, 1994). The BY55 antibody was evaluated in the 5th International Workshop on White Cell Differentiation Antigens, (*Leukocyte Typing V: White Cell Differentiation Antigens*, eds. Schlossman, S. F., Boumsell, L., Gilks, W., Harlan, J. M., Silverstein, R., Tedder, T. F., and Todd, R. F., (1995), Oxford University Press, Oxford, UK).

EXAMPLE II

Preparation of Antibody-PE Conjugate

Conjugation of IgG or IgM monoclonal antibody to PE was accomplished by 2-iminothiolane (IT) activation of PE and sulfosuccinimidyl 4-[N-maleimidomethyl]cyclohexane-1-carboxylate (sulfo-SMCC) activation of antibody as follows:

1. Activation of Monoclonal Antibody with sulfo-SMCC

For 20 mg of monoclonal antibody at a concentration of 36 mg/mL, 0.555 mL of monoclonal antibody concentrate were required. A 20 mg/mL solution of sulfo-SMCC in distilled water was prepared and used at an activation ratio of sulfo-SMCC: monoclonal antibody=15:1. Thus, to make a total volume of 1.000 mL, 0.100 mL of 1M phosphate buffer, 1M sodium chloride, pH 7.4 was mixed with 0.304 mL 1×PBS buffer, to which were added 0.555 mL of monoclonal antibody solution with stirring at room temperature and then slowly added 0.041 mL of sulfo-SMCC solution. The reaction mixture in a 15 mL tube was roller mixed at room temperature for 60 min and then, immediately applied to the top of a 30 mL G-50 Sephadex column, equilibrated with 1×Bis-Tris buffer (0.1M Bis-Tris, 0.1M sodium chloride, pH 5.55, pH adjusted with glacial acetic acid). The activated monoclonal antibody was eluted from the column with 1×Bis-Tris buffer and fractions of the first peak absorbing at 280 nm were collected. The sulfo-SMCC-monoclonal antibody concentration in mg/mL was determined by the $A_{280}$ value. The activated monoclonal antibody solution was diluted or concentrated to 2 mg/mL with Bis-Tris buffer.

2. Activation of PE with 2-iminothiolane

PE, R-phycoerythrin (red algae), obtained as a 60% ammonium sulfate suspension in 5 mM sodium phosphate, pH 7.0 buffer from Prozyme, Inc. (San Leandro, Calif.), was applied to a G-50 Sephadex column equilibrated with 50 mM phosphate, 2 mM EDTA, pH 7.0 buffer, eluted with the latter buffer, and then concentrated. For 34 mg of PE at a concentration of 74.38 mg/mL in 50 mM phosphate, 2 mM EDTA, pH 7.0 buffer, 0.457 mL of the PE concentrate were required. A 6 mg/mL solution of 2-iminothiolane hydrochloride (IT) was prepared and used at an activation ratio of IT:PE=15.7:1. Thus, to make a total volume of 0.850 mL, 0.085 mL of 1M phosphate buffer was mixed with 0.257 mL of 1×PE column buffer (0.1M phosphate, 0.1M sodium chloride, 0.1% sodium azide, 0.1 mM EDTA), to which were added 0.457 mL of PE solution with stirring at room temperature and then, slowly added 0.051 mL of IT solution. The reaction mixture in a 15 mL tube was roller mixed for 60 min, and then immediately loaded onto a 25 mL G-50 Sephadex column, equilibrated with Bis-Tris buffer. The activated PE was eluted from the column with 1×Bis-Tris buffer and the first peak off the column was collected. The concentration in mg/mL of activated PE was determined as $A_{565}/8.167$. The activated PE was diluted or concentrated to 3 mg/mL with 1×Bis-Tris buffer.

3. Conjugation of sulfo-SMCC-monoclonal antibody with iminothiolane-PE

For conjugation, equal volumes (9.0 mL) of activated monoclonal antibody at 2 mg/mL and activated PE at 3 mg/mL were mixed by adding activated monoclonal antibody into stirring activated PE, and then adding 0.360 mL of 1M phosphate buffer. The reaction mixture was roller mixed at room temperature for 1 hour. At the end of the mixing period, 0.918 mL of 25 mg/mL L-cysteine in DW were further added to the reaction mixture, which was roller mixed for an additional 15 min.

4. Purification of monoclonal antibody-PE conjugate

A Bio-Gel A 1.5 m column (10 mL of column per mg of monoclonal antibody or 200 mL) equilibrated with 1×PE column buffer was prepared. The sample was loaded onto the Bio-Gel A 1.5 m column, and eluted with 1×PE column buffer. The $A_{280}/A_{565}$ ratio was calculated for each fraction. All fractions with ratios from 0.43 until two fractions before the free PE eluates were pooled. For example, the pooled BB27-PE fractions were concentrated to a volume of 1.73 mL, less than 1% of the column volume, by using an Amicon YM30 membrane, diafiltering the concentrate with 1×PBS, 0.1% sodium azide, 0.1 mM EDTA buffer, and centrifuging the BB27-PE conjugate at 1800×g for 15 min at 4° C. A 50-fold dilution of this pooled sample gave $A_{565}$=0.6820 or (/8.167)×50=4.18 mg/mL PE and 7.22 mg total PE in the BB27-PE conjugate, and $A_{280}$=0.1883 or [0.6820/5.60 (PE's $A_{565}/A_{280}$)]×50=3.33 mg/mL BB27 and 5.75 mg total BB27 in the BB27-PE conjugate. The molar ratio of PE/BB27 is therefore (7.22 mg PE/240,000)//(5.75 mg BB27/160,000) =0.837. A corrected F/P ratio based on the formula, [$A_{280}/A_{565}$ (conjugate)−$A_{280}/A_{565}$ (dye)]×8.77, is 0.855.

Similar methods were used to prepare IL-12R-PE and BY55-PE conjugates having F/P ratios of 0.614 and 0.577, and corrected F/P ratios of 0.967 and 0.862, respectively.

EXAMPLE III

Preparation of Antibody-Aminodextran-PE Conjugates

The procedure was similar to the one used in U.S. Pat. No. 5,527,713 issued Jun. 18, 1996, to Bolton, et. al. to prepare conjugates of anti-CD3 antibody with aminodextran, either 1X-Amdex or 5X-Amdex. However, in the present work two different proteins, one, a monoclonal antibody and the other, a fluorescent protein, were conjugated simultaneously to the aminodextran. Trials with total protein, BB27 and PE, to 5X-Amdex weight ratios of 3:1 and about 1:1, and an antibody: 5X-Amdex weight ratio of 1:2 were carried out.

1. Activation of aminodextran with sulfo-SMCC 0.667 mL of a 10 mg/mL solution of 5X-Amdex in distilled water, to which 0.033 mL of 20×PBS buffer solution were added to make a 1×PBS solution, were activated with 0.120 mL of 10 mg/mL/mL sulfo-SMCC solution in 1×PBS. The mixture was roller mixed for about one hour at room temperature. After the mixing was completed, the reaction mixture was immediately applied to the top of a 25 mg/mL G-50 Sephadex column equilibrated with 1×PBS. The sample was eluted using 1×PBS and collected in about 2 mL fractions. Fractions of the first band absorbing at 280 nm contained the high molecular weight activated 5X-Amdex as was verified by Tyndall scatter with a focused visible light beam (Model 650, Cambridge Instruments, Inc., Buffalo, N.Y.). These fractions were pooled to give about 3.5 mL total sulfo-SMCC-activated 5X-Amdex, 1.75 mL used in each of two trials.

2. Activation of Antibody

BB27 monoclonal antibody as prepared above was activated by the addition of 0.065 mL of a 2 mg/mL solution of iminothiolane in 1×PBS and 0.324 mL 1×PBS to 0.278 mL of BB27 concentrate (36.00 mg/mL). The resulting solution which had an antibody concentration of 15 mg/mL and an iminothiolane molar activation ratio of 15 was mixed at ambient temperature for about one hour. The reaction mixture was then chromatographed on a 20 mL G-50 Sephadex column equilibrated with 1×PBS and the sample was eluted using 1×PBS. The first band peak fraction yielded about 2.5 mL of 3.519 mg/mL antibody solution which contained a total of 8.797 mg IT-BB27 antibody derivative.

3. Activation of PE

PE, R-phycoerythrin (red algae) from Prozyme, Inc., the 60% ammonium sulfate removed by buffer exchange by elution on a G-50 Sephadex column equilibrated with 50 mM phosphate, 2 mM EDTA, pH 7.0, and concentrated, was then activated by the addition of 0.097 mL of a 2 mg/mL solution of iminothiolane in 1×PBS and 0.089 mL 1×PBS to 0.189 mL of PE concentrate (79.27 mg/mL). The resulting solution which had a PE concentration of 40 mg/mL and an iminothiolane molar activation ratio of 22.5 was mixed at room temperature for about one hour. The reaction mixture was then applied to the top of a 20 mL G-50 Sephadex column equilibrated with 1×PBS and the sample was eluted with 1×PBS. The first band peak fraction gave about 3.8 mL of 2.523 mg/mL PE at an $A_{565}/A_{280}$ ratio of 5.0338, which contained a total of 9.587 mg IT-PE.

4. Conjugation of IT-BB27 and IT-PE to sulfo-SMCC-5X-Amdex

Trial 1—10 mg total protein: 3.333 mg 5X-Amdex 0.406 mL of 3.519 mg/mL IT-BB27 solution (about 1.429 mg antibody) were first mixed with 3.397 mL of 2.523 mg/mL IT-PE solution (about 8.571 mg PE), to which were added 1.750 mL of sulfo-SMCC-5X-Amdex solution (about 3.333 mg 5X-Amdex) and the entire mixture was roller mixed overnight for 16–24 hours.

Trial 2—3 mg total protein: 3.333 mg 5X-Amdex

In a similar way, 0.430 mL of 3.519 mg/mL IT-BB27 solution (about 1.5138 mg antibody) were first mixed with 0.600 mL IT-PE solution (about 1.5138 mg PE), to which were added 1.750 mL of sulfo-SMCC-5X-Amdex solution (about 3.333 mg 5X-Amdex) and the entire mixture was roller mixed overnight for 16–24 hours.

After the mixing was completed, the total volume of each mixture was determined and 0.120 times this volume of 5 mg/mL L-cysteine in 1×PBS was added to each conjugation mixture. The L-cysteine containing mixtures were then mixed for an additional 15 minutes to effect blocking of any unreacted sulfo-SMCC moieties. Lastly, 20 mg/mL iodoacetamide in 1×PBS in the amount of 0.120 times the total mixture volume and 1M borate buffer solution, pH 9.8, in the amount of 0.020 times the total mixture volume were added to each mixture. The resulting mixtures were mixed for about 30 minutes to block any unreacted sulfhydryl groups.

5. Purification of BB27-5X-Amdex-PE conjugates

The total volume of trial 1 conjugation mixture was reduced to about 1.5 mL by centrifuging an Amicon Centri-Prep 30 tube containing the sample for about 20 minutes at 2000 rpm using a refrigerated Beckman J-6B centrifuge. Trial 2 conjugation mixture was used without concentration at about 2.9 mL. The samples were placed on the top of a Bio-Gel A-5 m agarose column (2.5 cm×48 cm) equilibrated with 1×PBS and chromatographed using 1×PBS as eluant. Eluant fractions of about 4 mL volume were collected using a Pharmacia LKB FRAC-100 collector operating in the drop collection mode. The fractions were monitored using a LKB 2138 Uvicord S monitor operating at 280 nm. In trial 1, the first narrow, intense band eluted from the column contained the BB27-aminodextran-PE conjugate. A lower intensity shoulder of less than one-third the intensity of the first peak in trial 1 contained excess PE. A medium-to-low intensity well-separated third band was attributed to low molecular weight excess blocking reagents. Trial 2 did not show the narrow and intense first band but only an initial broad shoulder on the second band containing excess PE.

The fractions collected for the BB27-5X-Amdex-PE conjugate were analyzed spectrophotometrically at 565 and 280 nm using a 1 cm path length cell. The concentration of PE in mg/mL in the conjugate was derived from the absorbance at 565 nm by using the formula, $A_{565}/8.167$. The active BB27 antibody concentration in the conjugate was determined by an ELISA assay for IgG1 antibody. Data for fractions 21 to 25 under the first narrow peak in trial 1 are listed in Table I. In trial 2, seven fractions containing the most PE were pooled and concentrated to give the data shown in Table I.

TABLE I

| Fraction | $A_{565}$ | $A_{280}$ | $A_{565}/A_{280}$ | PE, mg/mL | BB27, µg/mL |
|---|---|---|---|---|---|
| 21 | 1.096 | 0.276 | 3.96 | 0.134 | 1.32 |
| 22 | 2.437 | 0.581 | 4.19 | 0.298 | 3.75 |
| 23 | 2.081 | 0.472 | 4.41 | 0.255 | 3.64 |
| 24 | 1.315 | 0.282 | 4.66 | 0.161 | 1.90 |
| 25 | 0.907 | 0.188 | 4.82 | 0.111 | 1.70 |
| trial 2 | 1.745 | 0.492 | 3.55 | 0.214 | 43.8 |

EXAMPLE IV

Preparation of BB27-1X-Amdex-PE Conjugate

The activation, conjugation, blocking, and chromatography procedures were the same as those described above for trial 1, BB27-5X-Amdex-PE conjugate. The concentrations of IT-PE (8.571 mg), IT-BB27 (1.429 mg), and sulfo-SMCC-1X-Amdex (3.333 mg) during conjugation were 0.973, 0.162, and 0.386 mg/mL, respectively. This time six fractions of the first narrow peak were analyzed at 565 and 280 nm using a 1 cm path length cell. The IT-PE ($A_{565}/A_{280}$) ratio was 5.356. Absorbance and concentration data for the six fractions are shown in Table II.

TABLE II

| Fraction | $A_{565}$ | $A_{280}$ | $A_{565}/A_{280}$ | PE, mg/mL |
|---|---|---|---|---|
| 19 | 0.329 | 0.080 | 4.14 | 0.040 |
| 20 | 1.072 | 0.241 | 4.45 | 0.131 |
| 21 | 1.423 | 0.313 | 4.55 | 0.174 |
| 22 | 1.258 | 0.267 | 4.70 | 0.154 |
| 23 | 1.023 | 0.209 | 4.89 | 0.125 |
| 24 | 0.863 | 0.172 | 5.01 | 0.106 |

EXAMPLE V

Preparation of BB27-5X-Amdex-PE Conjugates Using Column Buffer Instead of 1×PBS for PE Conjugate Purification and Storage The procedures were the same as those described above for trial 1, BB27-5X-Amdex-PE conjugate, except purification of the final conjugate was carried out on a Bio-Gel A-5 m agarose column equilibrated with column buffer, consisting of 1×PBS, 0.1 mM EDTA, 1 mM iodoacetamide, pH 7.2, and chromatographed with the same column buffer as eluant. In trial 3, the same amounts of IT-PE (8.571 mg), IT-BB27 (1.429 mg) were mixed with sulfo-SMCC-5X-Amdex (3.333 mg), as in trial 1, at concentrations of 2.23, 0.373, and 0.869 mg/mL, respectively, during conjugation. In trial 4, the same amounts of IT-PE, IT-BB27 as in trial 1, but 2× the amount of sulfo-SMCC-5X-Amdex (6.666 mg) were used at concentrations of 1.65, 0.275, and 1.28 mg/mL, respectively, during conjugation. The IT-PE ($A_{565}/A_{280}$) ratio was 5.790. Data for fractions collected under the first narrow peak in trials 3 and 4 are listed in Table III.

TABLE III

| Fraction | $A_{565}$ | $A_{280}$ | $A_{565}/A_{280}$ | PE, mg/mL | BB27, μg/mL |
|---|---|---|---|---|---|
| trial 3 | | | | | |
| 19 | 0.728 | 0.377 | 1.93 | 0.089 | 1.47 |
| 20 | 1.382 | 0.511 | 2.70 | 0.169 | 3.83 |
| 21 | 1.006 | 0.421 | 2.39 | 0.123 | 3.15 |
| 22 | 0.684 | 0.350 | 1.95 | 0.084 | 1.86 |
| trial 4 | | | | | |
| 20 | 1.043 | 0.441 | 2.37 | 0.128 | 2.11 |
| 21 | 0.986 | 0.425 | 2.32 | 0.121 | 2.76 |
| 22 | 0.765 | 0.374 | 2.04 | 0.094 | 1.50 |

EXAMPLE VI

Analyses for IgG1 and IgM Antibodies by ELISA

Following the method described in ENZYME-IMMUNOASSAY, E. T. Maggio, CRC Press, Boca Raton, Fla., 1985, pp 181–196, microtiter plates (Corning modified flat bottom ELISA plates) were coated with 100 μL of affinity-purified goat anti-mouse IgG1 or IgM (Southern Biotechnology Associates, Inc.), diluted to 0.6 μg/mL in 0.2M carbonate buffer, pH 9.6, overnight at 4° C. After washing with 1×PBS, pH 7.2, containing 0.05% Tween 20, the plates were saturated with PBS containing 1% BSA and incubated for 90 min at room temperature. Dilutions of antibody-5X-Amdex-PE conjugate samples were made in 1% BSA/PBS and 100 μL of each were added to the plate, which was then incubated for one hour at room temperature. Dilutions of the IgG1 and IgM antibody standards between 7.8 and 250 ng/mL, and 15.6 and 500 ng/mL, respectively, were used for calibration curves. After washing the plates, 100 μL of horseradish peroxidase(HRP)-conjugated goat anti-mouse Ig (Cappel), diluted in PBS were added and incubated for one hour at room temperature. The plates were washed and reactions were revealed by the addition of 200 μL of ABTS, 2,2'-azino-bis(3-ethylbenzthiazoline-6-sulfonic acid (Sigma), at 0.2 mg/mL in 0.2M sodium citrate buffer, pH 4.0, and 0.02% hydrogen peroxide. After a one hour incubation at room temperature, the plates were read on a V MAX microplate reader (Molecular Devices) at 405 nm using 490 nm as a reference wavelength. Semi-log plots of absorbance versus concentration were used to prepare IgG1 and IgM antibody standard linear regression curves. The antibody concentration in the samples was calculated by using absorbance values in the linear range of the standard curve.

EXAMPLE VII

Estimation of Molecular Weights of Antibody-Aminodextran-PE Conjugates

A mixture of gel filtration standards (Bio-Rad) or molecular weight markers (Sigma) and blue dextran (T-2M) was applied to the same A-5 m column that was used to purify the antibody-aminodextran-PE conjugates, eluted from the column with 1×PBS, monitored by $A_{280}$, and collected at the same drop count of 120 drops/fraction or about 4 mL/fraction. The curve obtained, when the logarithm of the molecular weights of the standards was plotted against the respective ratios of elution volume ($V_e$) to column void volume ($V_o$), was used by interpolation to estimate the molecular weights of antibody-aminodextran-PE conjugates. The void volume was determined from the position of antibody aggregates in the elution profile. The results are shown in Table IV for standards and conjugates collected in fractions 20 to 25, together with an upper limit on the PE/aminodextran molar ratio assuming PE (MW 240,000 daltons) were the only protein in the conjugate and 5X-Amdex with a MW of 350,000 daltons. In addition, fractions between 35 and 40, collected as a shoulder to the main band and showing some PE absorbance at 565 nm, are estimated from the semilog plot of molecular weight versus $V_e/V_o$ to contain species of molecular weight, 480,000 to 195,000 daltons, which are assigned to either excess PE or to a 1:1 PE:aminodextran conjugate.

TABLE IV

| | $V_e/V_o$ | MW, daltons | |
|---|---|---|---|
| blue dextran | 1.04 | ~2,000,000 | |
| thyroglobulin | 1.69 | 670,000 | |
| IgG | 2.15 | 158,000 | |
| ovalbumin | 2.41 | 44,000 | |
| myoglobin | 2.61 | 17,000 | |
| vitamin B-12 | 3.00 | 1,350 | |
| Fraction | | | PE/aminodextran |
| 20 | 1.026 | 2,000,000 | 6.9 |
| 21 | 1.077 | 1,850,000 | 6.3 |
| 22 | 1.128 | 1,750,000 | 5.8 |
| 23 | 1.179 | 1,650,000 | 5.4 |
| 24 | 1.231 | 1,500,000 | 4.8 |
| 25 | 1.282 | 1,400,000 | 4.4 |
| 30 | 1.54 | 920,000 | |
| 35 | 1.79 | 480,000 | |
| 40 | 2.05 | 195,000 | |

EXAMPLE VIII

Preparation of Anti-IL-12Rβ.44-5X-Aminodextran-PE Conjugates

The procedures were the same as those outlined for the preparation of the BB27-5X-Amdex-PE conjugate in trial 3 of EXAMPLE III, except anti-IL-12R antibody, also of the IgG1 class, was activated with IT and used in the conjugation instead of BB27 antibody. In trial 4, IT-PE (8.571 mg), IT-IL-12Rβ.44 (1.429 mg) were mixed with sulfo-SMCC-5X-Amdex (3.333 mg) at concentrations of 1.67, 0.279, and 0.651 mg/mL, respectively, during conjugation. In trial 5, the same amounts of reactants as in trial 4 were used, but 2× activation of 5X-Amdex with sulfo-SMCC was carried out, i.e., 0.120 mL of 10 mg/mL sulfo-SMCC solution in 1×PBS for 3.333 mg of 5X-Amdex. Concentrations of reactants during conjugation in trial 6 were 1.07, 0.178, and 0.415 mg/mL, respectively. The IT-PE ($A_{565}/A_{280}$) ratio was 5.866. Data for fractions collected under the first narrow peak in trials 5 and 6 are listed in Table V.

TABLE V

| Fraction | $A_{565}$ | $A_{280}$ | $A_{565}/A_{280}$ | PE, mg/mL | IL-12Rβ.44, μg/mL |
|---|---|---|---|---|---|
| trial 5 | | | | | |
| 20 | 1.015 | 0.428 | 2.37 | 0.124 | 1.55 |
| 21 | 2.178 | 0.677 | 3.22 | 0.267 | 4.55 |
| 22 | 1.630 | 0.549 | 2.97 | 0.200 | 4.15 |
| 23 | 0.992 | 0.410 | 2.42 | 0.121 | 1.98 |
| 24 | 0.721 | 0.351 | 2.06 | 0.088 | 1.79 |
| trial 6 | | | | | |
| 21 | 0.803 | 0.355 | 2.26 | 0.098 | 1.90 |
| 22 | 0.813 | 0.356 | 2.29 | 0.100 | 2.25 |
| 23 | 0.687 | 0.323 | 2.13 | 0.084 | 1.54 |

EXAMPLE IX

Preparation of Anti-BY55 Antibody-5X-Aminodextran-PE Conjugates

The procedures were the same as those outlined for the BB27-5X-Amdex-PE conjugate in trial 3 of EXAMPLE III, except BY55 antibody of the IgM class was activated with IT and used in the conjugation instead of BB27 antibody. In trial 7, the same amounts of reactants, IT-PE (8.571 mg), IT-BY55 (1.429 mg) were mixed with sulfo-SMCC-5X-Amdex (3.333 mg) at concentrations of 2.14, 0.357, and 0.833 mg/mL, respectively, during conjugation. In trial 8, 2× the usual amount of antibody was used so that reactants, IT-PE (8.571 mg), IT-BY55 (2.858 mg) were mixed with sulfo-SMCC-5X-Amdex (3.333 mg) at concentrations of 1.91, 0.637, and 0.743 mg/mL, respectively, during conjugation. The IT-PE ($A_{565}/A_{280}$) ratio was 5.800. Data for fractions collected under the first narrow peak in trials 7 and 8 are listed in Table VI.

TABLE VI

| Fraction | $A_{565}$ | $A_{280}$ | $A_{565}/A_{280}$ | PE, mg/mL | IL-12Rβ.44, μg/mL |
|---|---|---|---|---|---|
| trial 7 | | | | | |
| 20 | 1.338 | 0.549 | 2.44 | 0.164 | 3.43 |
| 21 | 2.506 | 0.817 | 3.07 | 0.307 | 7.50 |
| 22 | 1.596 | 0.541 | 2.95 | 0.195 | 4.78 |
| 23 | 0.874 | 0.363 | 2.41 | 0.107 | 3.10 |
| trial 8 | | | | | |
| 19 | 1.352 | 0.753 | 1.79 | 0.165 | 11.6 |
| 20 | 3.096 | 1.246 | 2.49 | 0.379 | 31.7 |
| 21 | 2.111 | 0.880 | 2.40 | 0.258 | 17.8 |
| 22 | 1.024 | 0.556 | 1.84 | 0.125 | 6.40 |

EXAMPLE X

Flow Cytometric Analyses of Whole Blood with BB27-PE and BB27-aminodextran-PE Conjugates BB27-PE and fractions of BB27-aminodextran-PE conjugates were titered, starting at either 2 μg or 1 μg per tube (in a 10 μl volume). Dilutions were added to 100 μl of whole blood and incubated for 1 hour at room temperature. Blood was lysed on a COULTER® Q-Prep (Coulter Corporation, Miami, Fla.), washed once with PBS and run on a flow cytometer (COULTER XL). When gated on the lymphocyte population, typical histograms show low PE mean channel fluorescence intensities close to the discriminator line for the labeled T cells because of the low BB27 receptor density (<1000 per cell) on the surface of the cells.

Figure 1A:
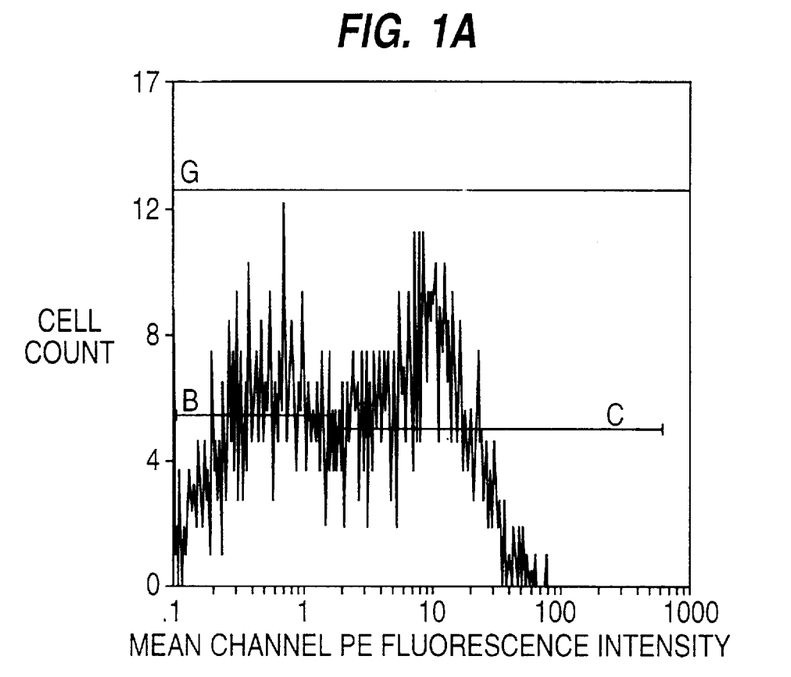
FIGS. 1A and 1B compare the fluorescence intensity of lymphocytes marked by the direct conjugate BB27-PE and by the aminodextran crosslinked conjugate BB27-5X-Amdex-PE, when each conjugate is mixed with whole blood.
Figure 1B:
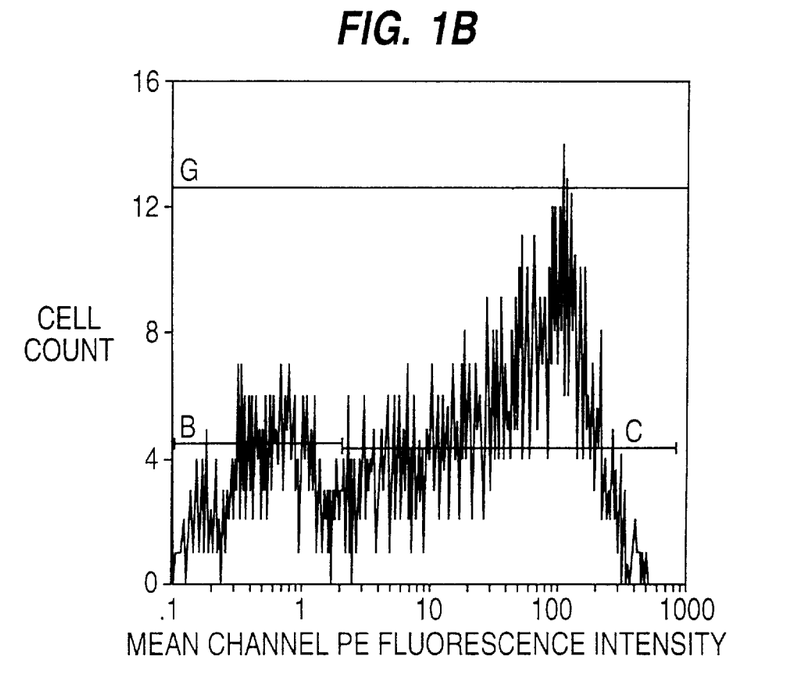
Figure 2A:
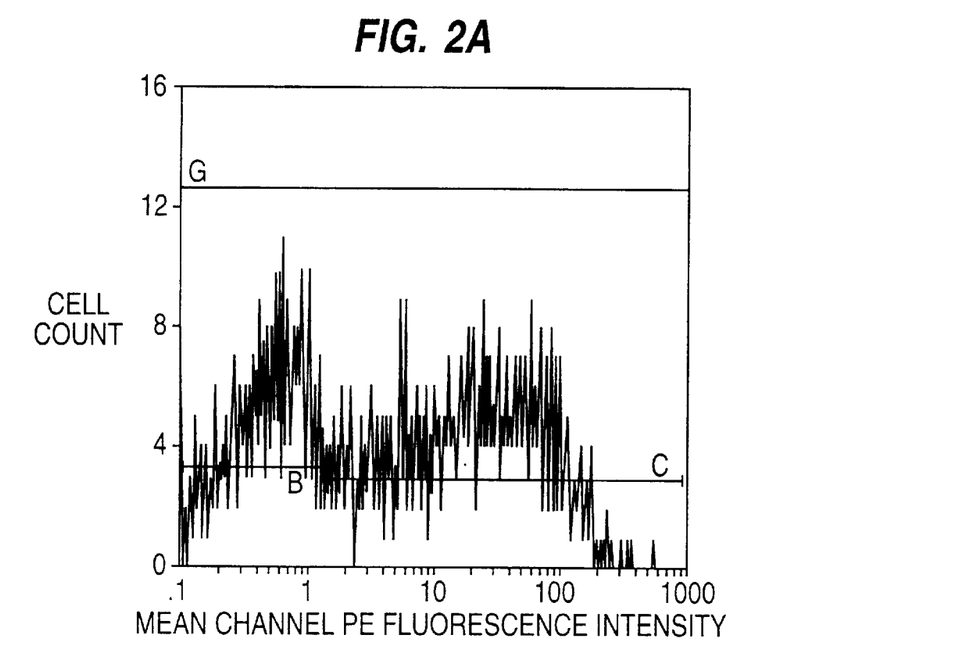
FIGS. 2A and 2B show histograms for lymphocytes in whole blood, either unblocked or blocked with free anti BB27 antibody, prior to mixing crosslinked conjugate BB27-5X-Amdex-PE with whole blood.
Figure 2B:
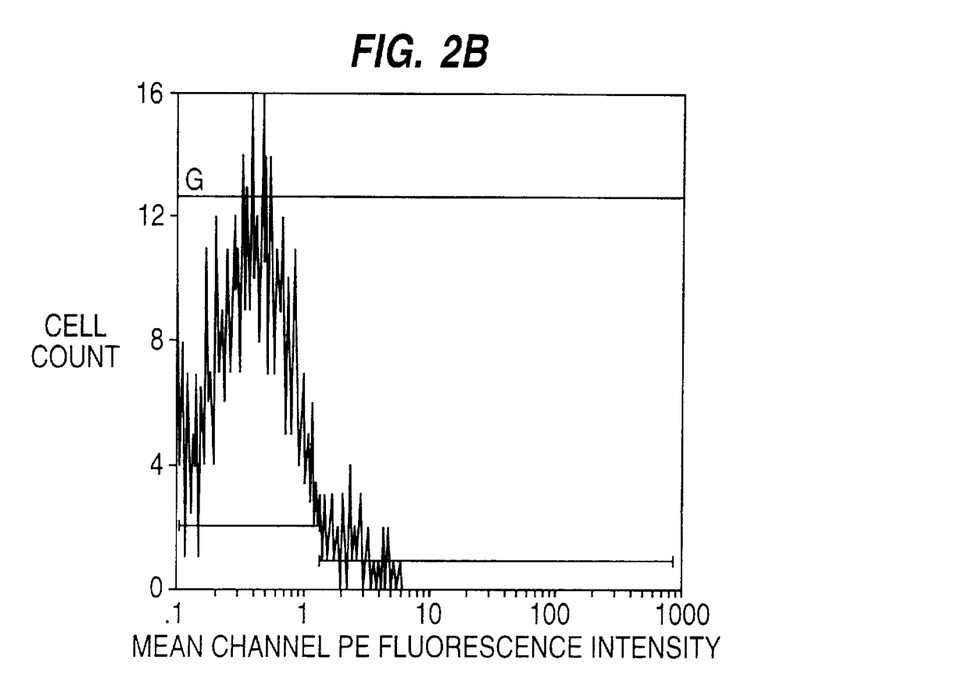

The utility of the BB27-5X-Amdex-PE conjugate as a marker containing more than two PE molecules per dextran molecule, compared to the direct BB27-PE conjugate which contains 0.85 PE molecule per antibody molecule, is shown in the histograms displayed in FIGS. 1A and 1B. FIGS. 1A and 1B show staining of scatter gated lymphocytes with BB27 antibody. 100 μl of whole blood from a normal donor was stained 10 μl containing 0.25 μg of BB27 antibody as (A) BB27-PE or (B) BB27-5X-Amdex-PE. FIGS. 1A and 1B shows that the crosslinked conjugate has 10-fold higher fluorescence intensity on BB27+ lymphocytes. Herein, the mean channel fluorescence intensity of labeled T cells could be enhanced up to 8-fold by using various fractions of trial 1, BB27-5X-Amdex-PE conjugate as the fluorescent marker. The effect of blocking BB27 receptor sites on targeted lymphocytes in whole blood with purified, unlabeled BB27 antibody (750 μg/ml) before using the BB27-5X-Amdex-PE marker is shown in the cell count versus PE fluorescent intensity histograms of FIGS. 2A and 2B. FIGS. 2A and 2B show staining of scatter gated lymphocytes with BB27 antibody. 100 μL of whole blood from a normal donor was stained with (FIG. 2A) 10 μL containing 0.25 μg of BB27 antibody in the form of BB27-5X-Amdex-PE or (FIG. 2B) BB27-5X-Amdex-PE, after blocking with an excess (750 μg/mL) of unlabeled BB27. FIGS. 2A and 2B shows that the conjugate is specific for the BB27 antigen. Titers of the control, BB27-PE, and the sample, BB27-5X-Amdex-PE, with whole blood were run with two blood donors. Mean channel PE fluorescence intensities and sample intensities relative to the control, obtained with the same instrument settings, are listed in Tables VII and VIII.

TABLE VII

| | Mean Channel PE Fluorescence Intensities | | | | |
|---|---|---|---|---|---|
| Donor 1 BB27, μg | Control | Fraction 22 | Fraction 23 | Fraction 24 | Fraction 25 |
| 2 | 14.2 | 73.6 | 53.0 | 54.5 | 39.3 |
| 1 | 12.8 | 71.6 | 53.1 | 48.5 | 39.6 |
| 0.5 | 11.7 | 77.2 | 60.8 | 42.2 | 41.1 |
| 0.25 | 10.4 | 78.6 | 56.8 | 48.1 | 43.4 |
| 0.125 | 10.2 | 74.7 | 65.4 | 45.5 | 50.2 |
| 0.0625 | 8.46 | 57.1 | — | 50.2 | 57.3 |
| 0.031 | 9.06 | 43.6 | 50.4 | 50.4 | 57.0 |
| | MFI Ratios, Fraction/Control | | | | |
| 2 | 1.0 | 5.2 | 3.7 | 3.8 | 2.8 |
| 1 | 1.0 | 5.6 | 4.1 | 3.8 | 3.1 |
| 0.5 | 1.0 | 6.6 | 5.2 | 3.6 | 3.5 |
| 0.25 | 1.0 | 7.6 | 5.5 | 4.6 | 4.2 |
| 0.125 | 1.0 | 7.3 | 6.4 | 4.5 | 4.9 |
| 0.0625 | 1.0 | 6.7 | — | 5.9 | 6.8 |
| 0.031 | 1.0 | 4.8 | 5.6 | 5.6 | 6.3 |

TABLE VIII

| | Mean Channel PE Fluorescence Intensities | | | | |
|---|---|---|---|---|---|
| Donor 2 BB27, μg | Control | Fraction 22 | Fraction 23 | Fraction 24 | Fraction 25 |
| 2 | 12.6 | 68.3 | 57.2 | 51.4 | 42.1 |
| 1 | 12.1 | 53.5 | 46.4 | 51.4 | 36.1 |
| 0.5 | 10.9 | 44.0 | 42.1 | 44.6 | 29.1 |
| 0.25 | 8.25 | 40.1 | 38.2 | 36.4 | 27.2 |
| 0.125 | 7.47 | 43.5 | 31.6 | 30.0 | 25.5 |
| 0.0625 | 7.96 | 37.8 | 28.4 | 27.7 | 19.5 |
| 0.031 | 6.90 | 28.5 | 31.4 | 23.6 | 20.6 |
| | MFI Ratios, Fraction/Control | | | | |
| 2 | 1.0 | 5.4 | 4.5 | 4.1 | 3.3 |
| 1 | 1.0 | 4.4 | 3.8 | 4.2 | 3.0 |

TABLE VIII-continued

Mean Channel PE Fluorescence Intensities

| Donor 2 BB27, μg | Control | Fraction 22 | Fraction 23 | Fraction 24 | Fraction 25 |
|---|---|---|---|---|---|
| 0.5 | 1.0 | 4.0 | 3.9 | 4.1 | 2.7 |
| 0.25 | 1.0 | 4.9 | 4.6 | 4.4 | 3.3 |
| 0.125 | 1.0 | 5.8 | 4.2 | 4.0 | 3.4 |
| 0.0625 | 1.0 | 4.7 | 3.6 | 3.5 | 2.4 |
| 0.031 | 1.0 | 4.1 | 4.6 | 3.4 | 3.0 |

As shown in tables VII and VIII, the antibody-aminodextran-phycoerythrin conjugates enhanced the fluorescence intensity of labeled T cells from 2 to 8-fold.

Data from the first donor were also used to evaluate fluorescence equivalent units (FEUs) by using COULTER Flow-Cal 575 beads, i.e., PE standard beads, to place the PE intensities on an absolute intensity scale. The 0.25 μg BB27 titers in the fluorescence intensity plateau region representing saturation of receptor sites for the four sample fractions and the 2 μg BB27 titer representing maximum fluorescence intensity for the control were used. Data are compiled in Table IX and used to calculate normalized FEUs and the number of PE molecules per molecule of dextran, knowing the PE per antibody in the direct BB27-PE conjugate and assuming PE fluorescence is not quenched by any interaction between PE molecules in the conjugate in which BB27 antibody and PE are crosslinked by dextran.

TABLE IX

| Sample | FEU units | FEU, normalized | PE/dextran or antibody |
|---|---|---|---|
| Fraction 22 | 117,093 | 5.641 | 4.8 |
| Fraction 23 | 90,500 | 4.360 | 3.7 |
| Fraction 24 | 71,526 | 3.446 | 2.9 |
| Fraction 25 | 64,355 | 3.100 | 2.7 |
| Control | 20,756 | 1.000 | 0.855 |

Note that the enhancement factors in the normalized FEU column represent a lower bound, assuming that the dextran crosslinked BB27-PE conjugate occupies a single receptor site like the direct BB27-PE conjugate. The difference between PE/dextran ratios for fractions 22 to 25 in Table IX and the upper bound ratios for the same fractions in Table IV gives an estimated one or two BB27 antibody/dextran ratio. Based on one or two BB27/dextran, the PE/dextran ratios at saturation, and the PE concentrations from Table I, the calculated BB27 antibody concentrations are up to ten-fold higher than the BB27 concentrations determined by ELISA and shown in Table I.

Similar flow cytometric data were obtained for the control, BB27-PE, and six fractions of BB27-1X-Amdex-PE, and are summarized in Tables X and XI.

TABLE X

Donor 1 Mean Channel PE Fluorescence Intensities

| BB27, μg | Control | Fraction 19 | Fraction 20 | Fraction 21 | Fraction 22 | Fraction 23 | Fraction 24 |
|---|---|---|---|---|---|---|---|
| 1 | 12.7 | 25.1 | 28.5 | 29.4 | 27.2 | 22.7 | 21.8 |
| 0.5 | 11.2 | 29.7 | 24.8 | 24.8 | 20.5 | 26.2 | 20.6 |
| 0.25 | 10.2 | 23.7 | 11.0 | 13.9 | 19.1 | 21.2 | 16.4 |
| 0.125 | 7.7 | 21.4 | 6.3 | — | 17.3 | — | 13.7 |

TABLE X-continued

Donor 1 Mean Channel PE Fluorescence Intensities

| BB27, μg | Control | Fraction 19 | Fraction 20 | Fraction 21 | Fraction 22 | Fraction 23 | Fraction 24 |
|---|---|---|---|---|---|---|---|
| 0.0625 | 6.6 | 15.9 | 4.9 | 11.6 | 12.9 | 20.2 | 11.6 |
| 0.031 | 6.2 | 11.4 | 5.3 | 8.9 | 10.3 | 13.4 | 11.4 |
| | | MFI Ratios, Fraction/Control | | | | | |
| 1 | 1.0 | 2.0 | 2.2 | 2.3 | 2.1 | 1.8 | 1.7 |
| 0.5 | 1.0 | 2.6 | 2.2 | 2.2 | 1.8 | 2.3 | 1.8 |
| 0.25 | 1.0 | 2.3 | 1.1 | 1.4 | 1.9 | 2.1 | 1.6 |
| 0.125 | 1.0 | 2.8 | 0.8 | — | 2.2 | — | 1.8 |
| 0.0625 | 1.0 | 2.4 | 0.7 | 1.8 | 2.0 | 3.1 | 1.8 |
| 0.031 | 1.0 | 1.8 | 0.9 | 1.4 | 1.7 | 2.2 | 1.8 |

TABLE XI

Donor 2 Mean Channel PE Fluorescence Intensities

| BB27, μg | Control | Fraction 19 | Fraction 20 | Fraction 21 | Fraction 22 | Fraction 23 | Fraction 24 |
|---|---|---|---|---|---|---|---|
| 1 | 10.6 | 24.5 | 27.8 | 25.9 | 21.3 | 18.7 | 19.8 |
| 0.5 | 8.1 | 21.6 | 21.2 | 18.9 | 17.6 | 20.3 | 18.8 |
| 0.25 | 9.1 | 19.4 | 19.7 | 17.2 | 18.1 | 19.4 | 14.9 |
| 0.125 | 7.9 | 19.8 | 16.6 | 14.5 | 13.4 | 15.8 | 14.8 |
| 0.0625 | 6.8 | 12.3 | 11.8 | 13.7 | 12.1 | 12.4 | 12.6 |
| 0.031 | 5.7 | 9.6 | 9.4 | 11.0 | 10.8 | 13.5 | 9.8 |
| | | MFI Ratios Fraction/Control | | | | | |
| 1 | 1.0 | 2.3 | 2.6 | 2.4 | 2.0 | 1.8 | 1.9 |
| 0.5 | 1.0 | 2.7 | 2.6 | 2.3 | 2.2 | 2.5 | 2.3 |
| 0.25 | 1.0 | 2.1 | 2.2 | 1.9 | 2.0 | 2.1 | 1.6 |
| 0.125 | 1.0 | 2.5 | 2.1 | 1.8 | 1.7 | 2.0 | 1.9 |
| 0.0625 | 1.0 | 1.8 | 1.7 | 2.0 | 1.8 | 1.8 | 1.9 |
| 0.031 | 1.0 | 1.7 | 1.6 | 1.9 | 1.9 | 2.4 | 1.7 |

The 0.5 μg BB27 titers in the six samples and the 1 μg titer for the control were used to evaluate FEUs using COULTER Flow-Cal 575 beads. Data are shown in Table XII.

TABLE XII

| | FEU units | | FEU, normalized | | PE/dextran or antibody | |
|---|---|---|---|---|---|---|
| Sample | Donor 1 | Donor 2 | Donor 1 | Donor 2 | Donor 1 | Donor 2 |
| Control | 19,726 | 17,342 | 1.0 | 1.0 | 0.85 | 0.85 |
| Fraction 19 | 43,930 | 31,856 | 2.2 | 1.8 | 1.9 | 1.5 |
| Fraction 20 | 36,626 | 31,259 | 1.9 | 1.8 | 1.6 | 1.5 |
| Fraction 21 | 31,558 | 25,297 | 1.6 | 1.5 | 1.4 | 1.3 |
| Fraction 22 | 30,216 | 25,893 | 1.5 | 1.5 | 1.3 | 1.3 |
| Fraction 23 | 38,713 | 29,918 | 2.0 | 1.7 | 1.7 | 1.5 |
| Fraction 24 | 30,663 | 27,682 | 1.5 | 1.6 | 1.3 | 1.4 |

Note the lower PE fluorescence enhancements and lower apparent PE-to-dextran molar ratios obtained on targeted T-cells in whole blood with BB27-1X-Amdex-PE (up to 2.2-fold over the control) compared to enhancements with BB27-5X-Amdex-PE (up to 5.6-fold). Although 1X-Amdex (1,000,000 dalton) has a higher average molecular weight than 5X-Amdex (350,000 dalton), 1X-Amdex also has a longer extended sugar polymer chain which can in its conjugate with PE and BB27 antibody bridge two or more receptor sites for BB27 antibody on the T cell surface. 5X-Amdex in its PE and BB27 antibody conjugate may not have the required chain length to bridge two or more receptor sites.

BB27-5X-Amdex-PE conjugates of trials 3 and 4 showed higher MFI ratios, fraction/control, for mean channel PE fluorescent intensities. For 0.15 to 0.009 μg of conjugate mixed with whole blood, lysed and quenched, the MFI ratios ranged from 2.9 to 10.9 with trial 3 conjugate and from 3.2 to 15.7 with trial 4 conjugate for two blood donors. For the 2× amount of sulfo-SMCC-5X-Amdex used in trial 4, MFI ratios obtained with this conjugate were about 1.5× higher and did indicate more PE per dextran conjugate. The larger amount of aminodextran used in the 2× preparation would also give a larger amount of higher molecular weight aminodextran capable of taking on more PE.

EXAMPLE XI

Flow Cytometric Analyses of Transfectant Cells with IL-12Rβ.44-PE and IL-12Rβ.44-aminodextran-PE Conjugates Because of very low fluorescent intensities, overlapping with the autofluorescent background of cells, from cells targeted in whole blood by the direct IL-12Rβ.44-PE conjugate, a transfectant cell line was used to compare fluorescent intensities of cells labeled with the direct versus aminodextran crosslinked IL-12Rβ.44-PE conjugate by flow cytometry. Titers of the control, IL-12Rβ.44-PE, and the samples, 1×IL-12Rβ.44-5X-Amdex-PE and 2×IL-12Rβ.44-5X-Amdex-PE, starting at 0.3 μg per tube, were run on IL-12R receptor transfectant cells (PB112) mixed 1:1 with untransfected parent cells (PB110) for a total number of $10^6$ cells/tube in a reaction volume of 200 μl. Cells were incubated for 1 hour at room temperature, washed once with PBS and analyzed by flow cytometry (COULTER XL). Mean channel PE fluorescence intensities and sample intensities relative to the control, obtained with the same instrument settings, are listed in Tables XIII and XIV.

TABLE XIII

| 1x conjugate | Mean Channel PE Fluorescence Intensities | | | |
|---|---|---|---|---|
| IL-12Rβ.44, μg | Control | Fraction 20 | Fraction 21 | Fraction 22 | Fraction 23 |
| 0.3 | 162.5 | 455. | 411.3 | 528. | 854.3 |
| 0.15 | 161.7 | 365.8 | 318.2 | 293.7 | 820.4 |
| 0.075 | 121.4 | 225.4 | 194.8 | 212.5 | 457.4 |
| 0.0375 | 97.3 | 185.7 | 94.1 | 143.9 | 398.9 |
| 0.019 | 67.7 | 102.9 | 79.2 | 99.3 | 195.2 |
| 0.009 | 41.5 | 82.5 | 53.6 | 46.3 | 101.2 |
| | MFI Ratios, Fraction/Control | | | | |
| 0.3 | 1.0 | 2.8 | 2.5 | 3.2 | 5.3 |
| 0.15 | 1.0 | 2.3 | 2.0 | 1.8 | 5.1 |
| 0.075 | 1.0 | 1.9 | 1.6 | 1.8 | 3.8 |
| 0.0375 | 1.0 | 1.9 | 1.0 | 1.5 | 4.1 |
| 0.019 | 1.0 | 1.5 | 1.2 | 1.5 | 2.9 |
| 0.009 | 1.0 | 2.0 | 1.3 | 1.1 | 2.4 |

TABLE XIV

| 2x conjugate | Mean Channel PE Fluorescence Intensities | | |
|---|---|---|---|
| IL-12Rβ.44, μg | Control | Fraction 21 | Fraction 22 | Fraction 23 |
| 0.3 | 162.5 | 144. | 131.8 | 146.9 |
| 0.15 | 161.7 | 121.6 | 111.2 | 122.1 |
| 0.075 | 121.4 | 65.5 | 58.6 | 61.9 |
| 0.0375 | 97.3 | 39.1 | 37.9 | 51.2 |
| 0.019 | 67.7 | 21.9 | 19. | 25.3 |
| 0.009 | 41.5 | 11.4 | 8.85 | 12.1 |

Fractions of the 1×IL-12Rβ.44-5X-Amdex-PE conjugate showed up to 5.3-fold amplification of PE fluorescent intensity over the direct IL-12Rβ.44-PE conjugate, when tested with transfected cells by flow cytometry. However, use of 2×-activated sulfo-SMCC-5X-Amdex in preparing the IL-12Rβ.44-5X-Amdex-PE conjugate showed no advantage in marker fluorescence intensity over the direct IL-12Rβ.44-PE conjugate (F/P ratio=0.967),which was used as the control. The greater degree of activation of 5X-Amdex in the 2× conjugate obviously resulted in considerably less PE in the same conjugate.

EXAMPLE 12

Flow Cytometric Analyses of Whole Blood with BY55-PE and BY55-aminodextran-PE Conjugates BY55 antibody conjugates were prepared to show the applicability of the method of fluorescence amplification with an IgM class antibody of much higher molecular weight, ~900,000 Daltons, compared to ~160,000 Daltons for IgG antibodies. Titers of the control, BY55-PE, and the samples, 1×BY55-5X-Amdex-PE and 2×BY55-5X-Amdex-PE, starting with 0.9 μg per tube (in 10 μl), with 100 μl whole blood, were run with one blood donor. Cells were incubated for 1 hour at room temperature, lysed on a COULTER Q-Prep, washed once with PBS and run on a flow cytometer (COULTER XL). Mean channel PE fluorescence intensities relative to the control, obtained with the same instrument settings, are listed in Tables XV and XVI.

TABLE XV

| 1x conjugate | Mean Channel PE Fluorescence Intensities | | | |
|---|---|---|---|---|
| BY55, μg | Control | Fraction 20 | Fraction 21 | Fraction 22 | Fraction 23 |
| 0.9 | 2.42 | 44.9 | 29.1 | 22.9 | 10.8 |
| 0.45 | 2.58 | 37.1 | 29.5 | 18.6 | 9.45 |
| 0.225 | 2.55 | 29.1 | 23.7 | 12. | 9.32 |
| 0.1125 | 1.95 | 28.8 | 24.1 | 10.5 | 7.33 |
| 0.0563 | 2.08 | 23. | 21.5 | 11.8 | 9.03 |
| | MFI Ratios, Fraction/Control | | | | |
| 0.9 | 1.0 | 18.6 | 12.0 | 9.5 | 4.5 |
| 0.45 | 1.0 | 14.4 | 11.4 | 7.2 | 3.7 |
| 0.225 | 1.0 | 11.4 | 9.3 | 4.7 | 3.7 |
| 0.1125 | 1.0 | 14.8 | 12.4 | 5.4 | 3.8 |
| 0.0563 | 1.0 | 11.1 | 10.3 | 5.7 | 4.3 |

TABLE XVI

| 2x conjugate | Mean Channel PE Fluorescence Intensities | | | |
|---|---|---|---|---|
| BY55, μg | Control | Fraction 19 | Fraction 20 | Fraction 21 | Fraction 22 |
| 0.9 | 2.42 | 21.9 | 29.4 | 15.0 | 9.95 |
| 0.45 | 2.58 | 25.2 | 20.7 | 13.9 | 7.33 |
| 0.225 | 2.55 | 27.2 | 14.4 | 12.7 | 7.51 |
| 0.1125 | 1.95 | 15.0 | 13.6 | 9.3 | 6.33 |
| 0.0563 | 2.08 | 13.6 | 10.5 | 9.5 | 2.42 |
| | MFI Ratios. Fraction/Control | | | | |
| 0.9 | 1.0 | 9.0 | 12.1 | 6.2 | 4.1 |
| 0.45 | 1.0 | 9.8 | 8.0 | 5.4 | 2.8 |
| 0.225 | 1.0 | 10.7 | 5.6 | 5.0 | 2.9 |
| 0.1125 | 1.0 | 7.7 | 7.0 | 4.8 | 3.2 |
| 0.0563 | 1.0 | 6.5 | 5.0 | 4.6 | 1.2 |

Data from the 1×BY55 conjugate, fractions 20 and 21, and the 2×BY55 conjugate, fractions 19 and 20, were also used to evaluate FEUs by using COULTER Flow-Cal 575 beads to place the PE intensities on an absolute scale. The results are shown in Table XVII.

TABLE XVII

| BY55, µg | FEU units Control | 1x, Frac 20 | 1x, Frac 21 | 2x, Frac 19 | 2x, Frac 20 |
|---|---|---|---|---|---|
| 0.9 | 22,601 | 405,546 | 263,114 | 198,208 | 265,818 |
| 0.45 | 24,044 | 335,231 | 266,720 | 287,956 | 187,390 |
| 0.225 | 23,773 | 263,113 | 214,434 | 245,986 | 130,597 |
| 0.1125 | 18,364 | 260,409 | 218,040 | 136,006 | 123,386 |
| 0.0563 | 19,536 | 208,124 | 194,602 | 123,386 | 95,440 |
| | | | FEU, normalized | | |
| 0.9 | 1.00 | 17.9 | 11.6 | 8.8 | 11.8 |
| 0.45 | 1.00 | 13.9 | 11.1 | 9.5 | 7.8 |
| 0.255 | 1.00 | 11.1 | 9.0 | 10.3 | 5.5 |
| 0.1125 | 1.00 | 14.2 | 11.9 | 7.4 | 6.7 |
| 0.0563 | 1.00 | 10.7 | 10.0 | 6.3 | 4.9 |
| | | | PE/dextran or antibody | | |
| 0.9 | 0.862 | 15.4 | 10.0 | 7.6 | 10.2 |
| 0.45 | 0.862 | 12.0 | 9.6 | 8.2 | 6.7 |
| 0.255 | 0.862 | 9.6 | 7.8 | 8.9 | 4.7 |
| 0.1125 | 0.862 | 12.2 | 10.2 | 6.4 | 5.8 |
| 0.0563 | 0.862 | 9.2 | 8.6 | 5.4 | 4.2 |

The corrected F/P or PE/antibody ratio of 0.862 for the direct BY55-PE conjugate was used to obtain PE/dextran ratios from normalized FEU values by multiplying each value by 0.862. The MFI ratios obtained for BY55-5X-Amdex-PE conjugates are similar to values obtained for BB27-5X-Amdex-PE conjugates in trials 3 and 4, and thus indicate that both IgM and IgG class antibody-5X-Amdex-PE conjugates can contain similar numbers of PE molecules per conjugate. Similarly, based on one or two BY55/dextran, the PE/dextran ratios at saturation from Table XVII, and the PE concentrations from Table VI, calculated BY55 concentrations are up to tenfold higher than BY55 concentrations determined by ELISA and shown in Table VI. The lower ELISA figures for both BB27 and BY55 antibodies in the aminodextran-crosslinked conjugates of antibody and PE probably reflect the relative inaccessibility of various antibody epitopes in the conjugates to the goat anti-mouse antibody used in the assay. Since the standard curve in this assay is generated using free antibody, the conjugate antibody concentrations are likely to be underestimated.

Figure 3A:
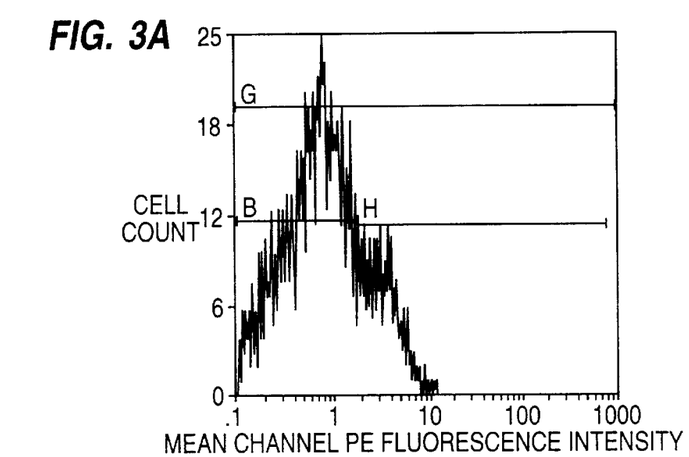
FIGS. 3A, 3B and 3C compare the fluorescence intensity of lymphocytes marked by the direct conjugate BY55-PE and by different fractions of the aminodextran crosslinked conjugate, BY55-5X-Amdex-PE, when each conjugate is mixed with whole blood.
Figure 3B:
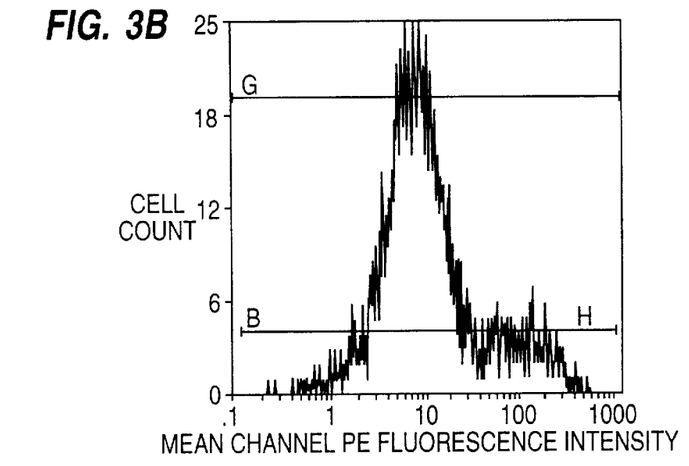
Figure 3C:
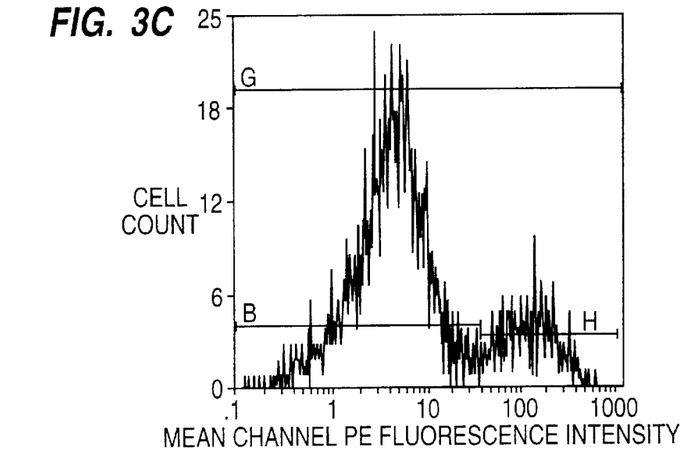
Figure 4A:
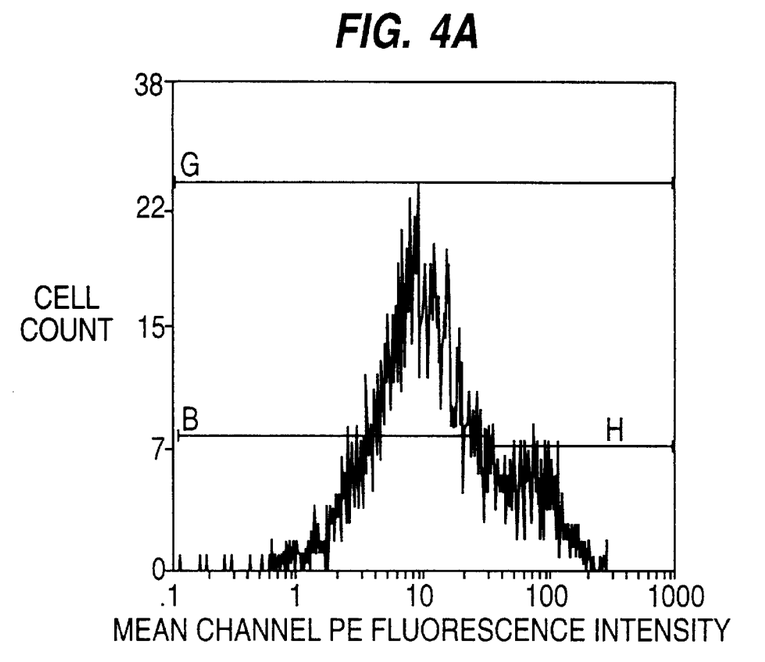
FIGS. 4A and 4B show histograms for lymphocytes in whole blood, either unblocked or blocked with free anti-BY55, prior to mixing crosslinked conjugate BY55-5X-Amdex-PE with whole blood.
Figure 4B:
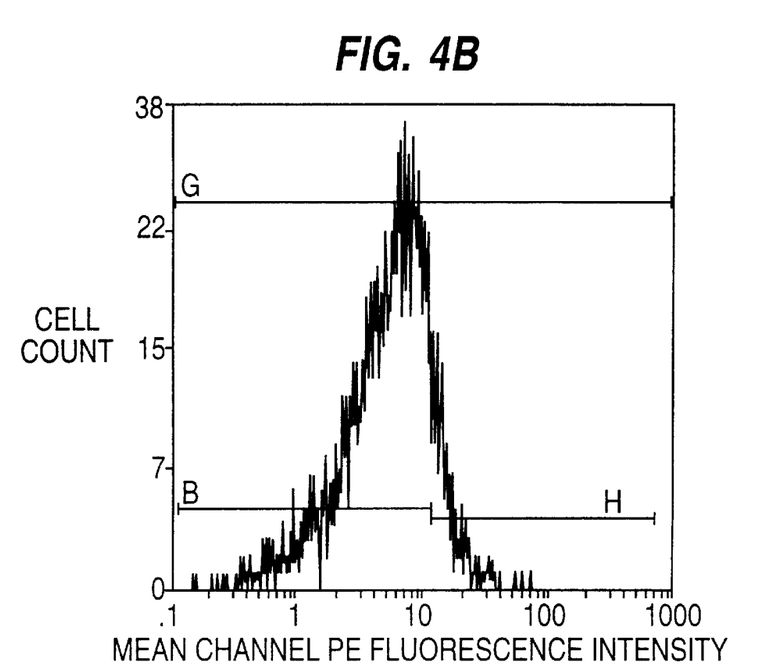
Figure 5A:
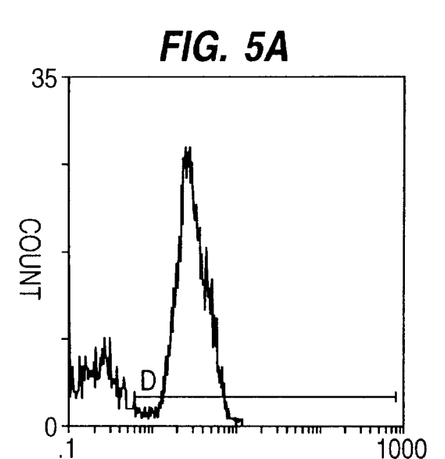
FIGS. 5A–5F are histograms which show the fluorescence intensity of lymphocytes stained simultaneously with CD4-FITC, BB27-PE, and CD8-ECD compared to lymphocytes stained simultaneously with CD4-FITC, BB27-5X-Amdex-PE and CD8-ECD, when each set of markers is mixed with whole blood.
Figure 5B:
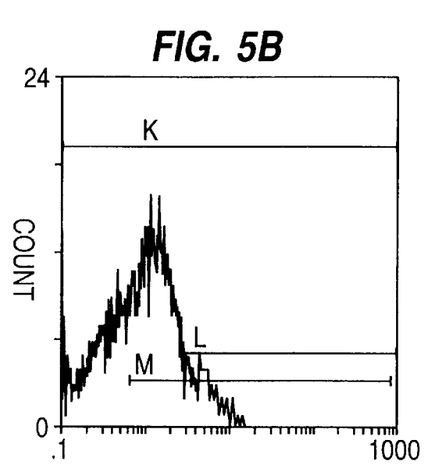
Figure 5C:
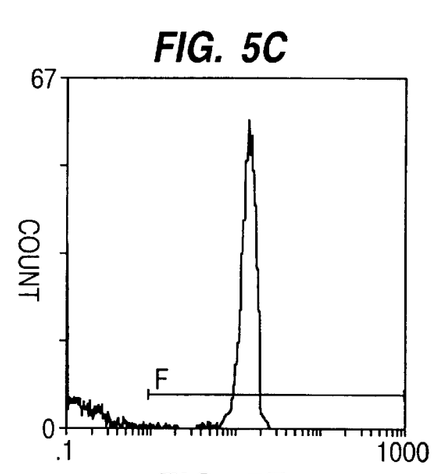
Figure 5D:
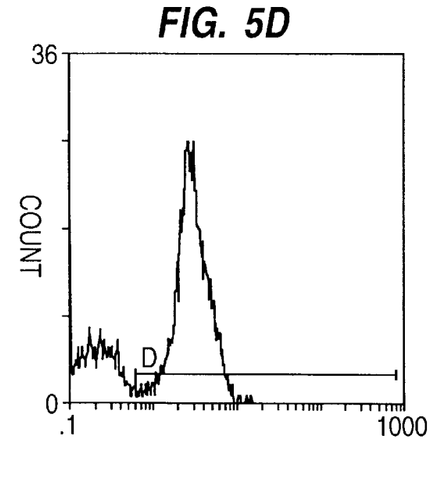
Figure 5E:
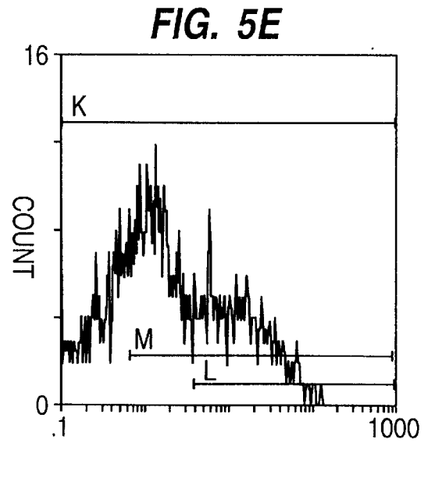
Figure 5F:
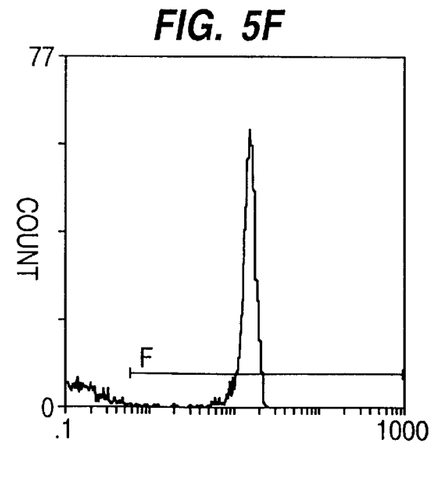

The much greater resolution of targeted BY55+ cells in whole blood with the 5X-Amdex-crosslinked BY55-PE conjugates, 1× Fraction 20 and 2× Fraction 19, compared to the direct BY55-PE conjugate is clearly evident for another blood donor in FIGS. 3A and 3B, in which the cell count versus PE fluorescent intensity histogram, gated on lymphocytes in the FS versus SS histogram, is shown for each marker. FIGS. 3A and 3B represent staining of scatter gated lymphocytes with BY55 antibody. 100 µL of whole blood from a normal donor was stained with 10 µL containing 0.25 µg of BY55 as (FIG. 3A) BY55-PE, (FIG. 3B) BY55-5X-Amdex-PE, 1×/fraction 20 or (C) BY55-5X-Amdex-PE, 2×/fraction 19. FIGS. 3A, 3B and 3C shows that the crosslinked conjugate has 30-fold higher fluorescence intensity on BY55+ lymphocytes. The large autofluorescence signals, centered at mean channel PE fluorescent intensities of 0.625, 6.60, and 3.36, and the BY55+ cell signals at 3.67, 75.4, and 90.0 for BY55-PE direct conjugate, 1× Fraction 20, and 2× Fraction 19, respectively, are best resolved for the 2× Fraction 19 sample, in which, according to the PE/dextran ratios, the conjugate contains one additional IgM and about four fewer PE per conjugate compared to the 1× Fraction 20 sample. Proportionally more IgM antibody in the conjugate may give less background fluorescence due to better presentation of the antibody and, thus, greater specificity of conjugate for targeted cells, and, at the same time, less non-specific binding of the conjugate to other cells. The specificity of the binding is shown in FIGS. 4A and 4B, in which lymphocytes from a third donor are stained with and without previous blocking by 7500 µg/ml unlabeled BY55 antibody. FIGS. 4A and 4b show staining of scatter gated lymphocytes with BY55 antibody. 100 µL of whole blood from a normal donor was stained with (FIG. 4A) 10 µL containing 0.25 µg of BY55 antibody in the form of BY55-5X-Amdex-PE, 2×/fraction 19 or (FIG. 4B) BY55-5X-Amdex-PE, 2×/fraction 19, after blocking with an excess (750 µg/mL) of unlabeled BY55. FIGS. 4A and 4B shows that the conjugate is specific for the BY55 antigen.

EXAMPLE XIII

Use of Antibody-Dextran-Phycoerythrin Conjugates in Multi-Color Staining

To determine whether the increased mass of the antibody-dextran-phycoerythrin conjugates would sterically hinder binding of specific antibodies to other cell surface antigens, BB27-5X-Amdex-PE (fraction 23) was incubated simultaneously with CD4-FITC and CD28-ECD. The CD4, CD28 and BB27 antigens are expressed on CD4+ T cells which are functionally distinct from CD4+CD28+BB27-cells (Gouttefangeas et. al., *Int. Immunol.* 6(3)423, 1994). Antibodies were incubated with 100 µl whole blood for 1 hour at a concentration of 0.25 µg each per test in a total volume of 110 µl. Blood was lysed on a COULTER Q-Prep, washed once with PBS and run on a flow cytometer (COULTER XL). When gated on the lymphocyte population, single parameter histograms (FIGS. 5A–5F) show the enhanced signal produced by staining with BB27-5X-Amdex-PE compared to staining with BB27-PE. FIGS. 5A–5F shows multicolor analysis using three markers. FIGS. 5A–5F show that that enhanced signal are obtained even when multiple markers are used. There was no difference in the binding of irrelevant antibodies CD4 and CD28, as demonstrated by the similarity in mean fluorescence intensity peak positions for these antibodies in the presence of BB27-5X-Amdex-PE or BB27-PE. This indicated that the increased mass of BB27-5X-Amdex-PE, compared to BB27-PE, does not affect the binding of other antibodies to cell surface antigens, thus expanding the potential use of this invention to multicolor flow cytometric analysis.

All publications cited in this specification are indicative of the level of skill of those in the art to which this application pertains. Each publication is individually incorporated herein by reference in the location where it is cited.

While the invention has been described with reference to a particularly preferred embodiment, it will be appreciated that modifications can be made without departing from the spirit of the invention. Such modifications are intended to fall within the scope of the appended claims.

We claim:

1. An antibody-aminodextran-phycobiliprotein conjugate, which conjugate contains two to twenty phycobiliproteins per aminodextran molecule, wherein said aminodextran has a degree of substitution with 1,3-diaminopropane of $\frac{1}{40}$ to $\frac{1}{8}$.

2. The conjugate of claim 1, wherein the antibody is selected from the group consisting of BB27, BY55, and IL12.

3. The conjugate of claim 1, wherein the phycobiliprotein is R-phycoerythrin.

4. The conjugate of claim 1, wherein the aminodextran is 5X-aminodextran.

5. The conjugate of claim 1, wherein the aminodextran is 1X-aminodextran.

6. A method of preparing an antibody-aminodextran-phycobiliprotein conjugate which method comprises the steps of:

(a) activating the antibody with iminothiolane, then purifying the activated antibody;

(b) activating the phycobiliprotein with iminothiolane, then purifying the activated phycobiliprotein;

(c) combining the activated and purified antibody and phycobiliprotein;

(d) activating the aminodextran with sulfosuccinimidyl 4-[N-maleimidomethyl]cyclohexane-1-carboxylate, then purifying the activated aminodextran;

(e) mixing all activated components together for about 16–24 hours to provide an antibody-aminodextran-phycobiliprotein conjugate; and (f) purifying the conjugates resulting from step (e).

7. The method of claim 6, wherein the antibody is selected from the group consisting of BB27, BY55, and IL12.

8. The method of claim 6, wherein the phycobiliprotein is R-phycoerythrin.

9. The method of claim 6, wherein the aminodextran is 5X-aminodextran.

10. The method of claim 6, wherein the aminodextran is 1X-aminodextran.

11. The method of claim 6, wherein the mixture is purified by size exclusion chromatography.

12. A method of detecting biological substances in an assay, which method comprises the steps of:

(a) mixing an antibody-aminodextran phycobiliprotein conjugate with a sample containing the substance to be detected to allow the antibody of such conjugate to couple to the substance to form a complex, wherein said conjugate contains two to twenty phycobiliprotein molecules per aminodextran molecule, and the aminodextran has a degree of substitution with 1,3-diaminopropane of $\frac{1}{40}$ to $\frac{1}{8}$;

(b) exciting each phycobiliprotein molecule of the complex to cause it to fluoresce; and (c) detecting the fluorescence signal from the complex to detect the substance coupled thereto via said antibody.

13. The method of claim 12, wherein the antibody is selected from the group consisting of BB27, BY55, and IL12.

14. The method of claim 12, wherein the phycobiliprotein is R-phycoerythrin.

15. The method of claim 12, wherein the dextran is 5X-aminodextran.

16. The method of claim 12, wherein the dextran is 1X-aminodextran.

17. The method of claim 12, wherein the phycobiliprotein is irradiated by excitation radiation.

18. The method of claim 12, wherein the fluorescent light emission is measured by flow cytometric analysis.

* * * * *